United States Patent
Forthmann et al.

(10) Patent No.: US 8,059,787 B2
(45) Date of Patent: Nov. 15, 2011

(54) SPECTRUM-PRESERVING HEEL EFFECT COMPENSATION FILTER MADE FROM THE SAME MATERIAL AS ANODE PLATE

(75) Inventors: Peter Forthmann, Sandesneben (DE); Roland Proksa, Hamburg (DE)

(73) Assignee: Koninklijke Philips Electronics N.V. (NL)

( * ) Notice: Subject to any disclaimer, the term of this patent is extended or adjusted under 35 U.S.C. 154(b) by 111 days.

(21) Appl. No.: 12/523,164

(22) PCT Filed: Jan. 23, 2008

(86) PCT No.: PCT/IB2008/050243
§ 371 (c)(1),
(2), (4) Date: Jul. 15, 2009

(87) PCT Pub. No.: WO2008/090518
PCT Pub. Date: Jul. 31, 2008

(65) Prior Publication Data
US 2010/0098209 A1    Apr. 22, 2010

(30) Foreign Application Priority Data
Jan. 26, 2007 (EP) .................................. 07101250

(51) Int. Cl.
*G21K 3/00* (2006.01)
(52) U.S. Cl. ........................ 378/156; 378/121
(58) Field of Classification Search .......... 378/156–159, 378/4, 16, 119, 121, 140, 143, 145
See application file for complete search history.

(56) References Cited

U.S. PATENT DOCUMENTS

| 5,033,075 A | 7/1991 | DeMone et al. | 378/156 |
| 5,166,966 A | 11/1992 | Steinmeyer | 378/156 |
| 6,968,042 B2 | 11/2005 | Toth et al. | 378/156 |
| 7,020,243 B2 | 3/2006 | Hsieh | 378/62 |
| 2006/0058974 A1 | 3/2006 | Lasiuk et al. | 702/97 |
| 2006/0256925 A1* | 11/2006 | Virshup et al. | 378/158 |

FOREIGN PATENT DOCUMENTS

| WO | 2005010916 A2 | 2/2005 |
| WO | 2005092195 A1 | 10/2005 |

OTHER PUBLICATIONS

Mori, S., et al.; Prototype heel effect compensation filter for cone-beam CT; 2005; Phys. Med. Biol.; 50:N359-N370.
Moore, C. J., et al.; Cone beam CT with zonal filters for simultaneous dose reduction, improved target contrast and automated set-up in radiotherapy; 2006; Phys. Med. Biol.; 51:2191-2204.

* cited by examiner

*Primary Examiner* — Courtney Thomas

(57) ABSTRACT

It is described a filter (300) for at least partially compensating for an X-ray tube (10) the target angle heel effect and preserving the tungsten spectrum of the X-rays. The filter (300) has an anode side (302) and a cathode side (304), wherein the cathode side (304) has a higher attenuation coefficient than the anode side (302). The attenuation coefficient is determined to at least partially compensate for the target angle heel effect. The filter (300) is from the same material as an anode plate (110) or the anode (108) of the X-raysource (10) which is usually tungsten or a tungsten alloy.

20 Claims, 1 Drawing Sheet

Figure 1:
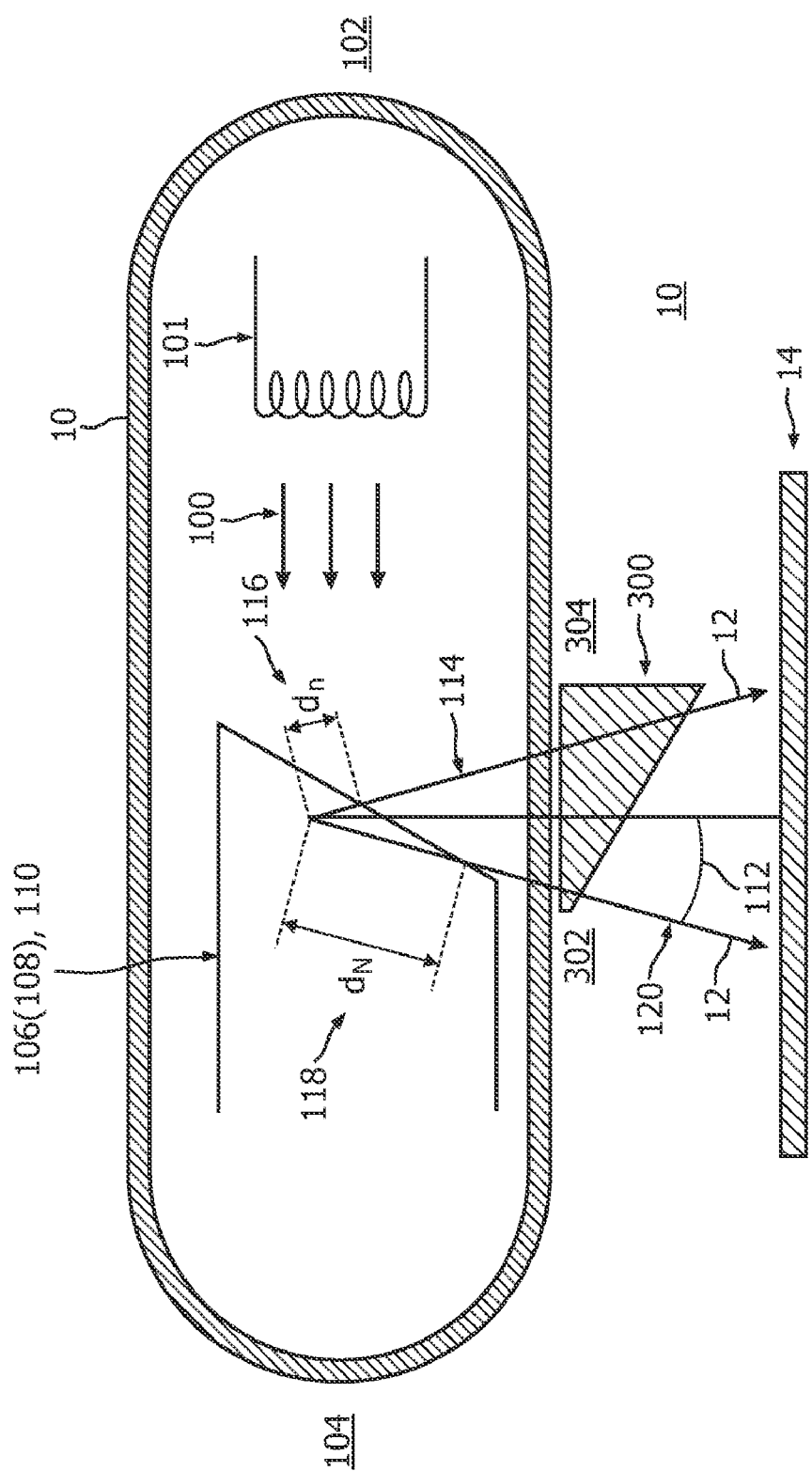

SPECTRUM-PRESERVING HEEL EFFECT COMPENSATION FILTER MADE FROM THE SAME MATERIAL AS ANODE PLATE

FIELD OF THE INVENTION

This invention relates generally to heel effect compensation filters, X-ray tubes and Computed Tomography (CT) imaging systems, and more particularly, to target angle heel effect compensation.

ART BACKGROUND

In known CT systems X-rays are generated by directing a beam of accelerated electrons at an anode plate typically of tungsten. A certain depth of penetration is associated with the X-ray generation in the anode, so that the emitted radiation passes varying amounts of anode material before leaving the plate.

As a consequence, the intensity and the spectrum of the generated radiation show a cone-angle dependent variation, leading to detector row dependent beam hardening and intensity, the so-called well known heel effect.

Especially for cone angles spanned by the upcoming 256 row detectors, this heel effect is significant and needs to be corrected, so as to avoid image artifacts. An X-ray tube source generally includes an anode side and a cathode side. The anode side is also known as the target, which is bombarded with electrons to generate X-ray beam radiation. X-rays from the X-ray tube are generated at a small depth inside the target (anode) of the X-ray tube. X-rays traveling toward the anode side of an object being scanned travel through more volume of the target than X-rays traveling toward a cathode side of the object. Therefore, X-rays traveling toward the anode side leave the target more attenuated than X-rays traveling toward the cathode side.

Mori et al. introduce a heel effect compensating filter, which is placed in front of an X-ray beam and has a varying thickness along a anode-cathode direction or so-called z-direction. The filter is made of aluminum and is designed to equalize the beam intensity along the said direction. However, the filter can not correct the spectral distortions mentioned above (Mori et al., Prototype heel effect compensation filter for cone-beam CT, Phys. Med. Biol., 50 (2005) N359-N370).

As illustrated in U.S. Pat. No. 6,968,042 a filter with an anode side and a cathode side between an X-ray source and an X-ray detector, has a higher attenuation coefficient on the cathode side than on the anode side. The attenuation coefficient is determined to at least partially compensate for the target angle heel effect. The filter material is aluminum, copper, titanium or beryllium. However, due to the chosen material, the filter can not correct the spectral distortions mentioned above.

SUMMARY OF THE INVENTION

In order to at least partially compensate the heel effect and additionally obtain a constant spectrum, a filter is provided that is made from the same material as the anode plate. Due to the small electron penetration depth in the anode material however, the compensation filter needs to be very thin.

The production process of such a filter could be facilitated with some form of carefully controlled thin film deposition technique like sputtering or some other epitactical process. Constant-thickness deposition with subsequent controlled mechanical, chemical and/or laser abrasion is another aspect of the invention to form the thin film thickness gradient.

In another aspect, a method of at least partially compensating for an X-ray tube target angle heel effect is provided. The method includes positioning a filter and comprises depositing a material on an X-ray tube window to form the filter, wherein the said material is the same as the material of an anode plate of the X-ray source.

In other aspects, an X-ray tube, an imaging system for scanning an object, and a Computed Tomography (CT) imaging system for scanning an object are provided. All embodiments includes a filter, wherein the material of the filter is the same as the material of an anode plate of the X-ray source.

While the invention has been described in terms of various specific embodiments, those skilled in the art will recognize that the invention can be practiced with modification within the spirit and scope of the claims.

This need may be met by the subject matter according to the independent claims. Advantageous embodiments of the present invention are described by the dependent claims.

At this point it has to be pointed out that the described method for is not used for providing a diagnosis or treating patients. The described method and all other aspects and embodiments of the present inventing merely provide additional and more detailed information, which may assist a physician in reaching a diagnosis and/or in deciding about appropriate therapy procedures.

It has to be noted that embodiments of the invention have been described with reference to different subject matters. In particular, some embodiments have been described with reference to apparatus type claims whereas other embodiments have been described with reference to method type claims. However, a person skilled in the art will gather from the above and the following description that, unless otherwise noted, in addition to any combination of features belonging to one type of subject matter also any combination between features relating to different subject matters, in particular between features of the apparatus type claims and features of the method type claims is considered to be disclosed with this application.

The aspects defined above and further aspects of the present invention are apparent from the example of one embodiment to be described hereinafter and are explained with reference to the example of the embodiment. The invention will be described in more detail hereinafter with reference to the example of the embodiment but to which the invention is not limited.

DETAILED DESCRIPTION OF THE DRAWING

The FIG. 1 shows a filter and illustrates the target angle and the heel effect.

Electrons 100 travel inside X-ray tube 10 from a cathode side 102 of a cathode 101 to an anode side 104 and collide with a target 106 in form of an anode 108, particularly an anode plate 110. The electrons 100 make contact with target 106 at different locations along target 106, and cause the emission of X-rays 12 at different angles on leaving target 106. The angle between target 106 and the perpendicular to X-ray detector rows 14 is a target angle 112. An X-ray 114 emitted from target 106 travels a distance dn 116 within target 106 before exiting target 106 toward cathode side 102. This is a shorter distance than a distance dN 118 that an X-ray 120 travels within target 106 before exiting target 106 toward anode side 104. Since dN 118 is greater than dn 116, then X-ray 120 leaves target 106 more attenuated than X-ray 114. This difference in attenuation is the heel effect. Further, the figure illustrates a heel effect compensation filter 300 in a cross-sectional view at isocenter. Filter 300 includes an anode side 302 and a cathode side 304. Filter 300 is entirely made of tungsten. In an alternative embodiment filter 300 is a tungsten alloy. The filter 300 is always of the same material as the anode 108, particularly its anode plate 110. As seen in the cross-sectional view, filter 300 is thicker on cathode side 304 than on anode side 302. In an exemplary embodiment cathode side 304 of the filter is about 200 μm thicker than anode side 302 of portion 208. In other embodiments the thickness difference is between about 50 μm mm and about 500 μm.

Because the cathode side 304 is thicker than the anode side 302, X-rays passing through cathode side 304 are more attenuated by the filter than X-rays passing through anode side 302 which compensates at least partially for the heel effect.

Exemplary embodiments of a wedge shaped heel effect compensation filter are described in U.S. Pat. No. 6,968,042 B2 in detail, which is hereby incorporated in its entirety. The assemblies are not limited to the specific embodiments described herein, but rather, components of each assembly may be utilized independently and separately from other components described herein.

It should be noted that the term "comprising" does not exclude other elements or steps and the "a" or "an" does not exclude a plurality. Also elements described in association with different embodiments may be combined. It should also be noted that reference signs in the claims should not be construed as limiting the scope of the claims.

The invention claimed is:

1. A method of at least partially compensating for an X-ray tube target angle heel effect, said method comprising:
positioning a filter having an anode side and a cathode side between an X-ray source and an X-ray detector, wherein the cathode side has a higher attenuation coefficient than the anode side, and wherein the attenuation coefficient is determined to at least partially compensate for the target angle heel effect; wherein said positioning a filter comprises depositing a material on an X-ray tube window to form the filter, wherein the said material is the same as the material of an anode plate of the X-ray source.

2. The method of claim 1, where the cathode side is thicker than the anode side by a value of about 50 μm to about 500 μm.

3. The method of claim 2, where the value is about 200 μm.

4. The method of claim 1, where the depositing a material on an X-ray tube window to form the filter comprises sputtering the material upon the X-ray tube window.

5. The method of claim 1, wherein said positioning a filter comprises depositing a material on the outside of an X-ray tube window to form the filter.

6. An X-ray tube comprising:
an anode with an anode plate;
a cathode;
a window; and
a material deposited on said window, wherein said material is wedge shaped; wherein said wedge shape comprises a horizontal top, a bottom, a first vertical side and a second vertical side and wherein said first vertical side and said second vertical side are unequal in length, wherein the said material is the same as the material of the said anode plate.

7. The x-ray tube of claim 6, where the window is flat and where the material is disposed such that the horizontal top and flat window touch along the horizontal top.

8. The x-ray tube of claim 6, where electrons travel from the cathode to the anode plate and where a section of the anode plate upon which the electrons collide with is not perpendicular with the cathode such that the electrons do not reflect from the anode plate at the same time.

9. The x ray tube of claim 6, where the filter is of a single attenuation portion.

10. The x-ray tube of claim 9, where electrons travel from the cathode to an anode plate of the X-ray source and where a section of the anode plate upon which the electrons collide with is not perpendicular with the cathode such that the electrons do not reflect from the anode plate at the same time.

11. The x-ray tube of claim 10, where the window is flat, where the filter has a horizontal top, and where the filter is disposed such that the horizontal top and flat window touch along the horizontal top.

12. The x-ray tube of claim 11, where the material is a tungsten alloy.

13. The x-ray tube of claim 12, where a cathode side of the filter is about 200 μm thicker than an anode side of the filter.

14. A Computed Tomography (CT) imaging system for scanning an object comprising;
an X-ray source having an anode and a cathode;
an X-ray detector to receive X-rays from said X-ray source;
a computer operationally coupled to said X-ray source and said X-ray detector; and
a filter having an anode side and a cathode side, positioned between said anode and said detector, wherein said cathode side has a higher attenuation coefficient than said anode side, wherein the attenuation coefficient is determined to at least partially compensate for a target angle heel effect, wherein said filter being positioned includes depositing a material on an X-ray tube window to form the filter, and wherein the said material is the same as the material of an anode plate of the said anode.

15. A filter for at least partially compensating for an X-ray tube target angle heel effect, comprising:
an anode side; and
a cathode side, wherein the cathode side has a higher attenuation coefficient than the anode side, wherein the attenuation coefficient is determined to at least partially compensate for the target angle heel effect; wherein the filter is from the same material as an anode plate of an X-ray source, and wherein the material is sputtered on a film.

16. The filter of claim 15, where a thickness gradient of the film is controlled at least by mechanical means.

17. The filter of claim 15, where a thickness gradient of the film is controlled at least by chemical means.

18. The filter of claim 15, where a thickness gradient of the film is controlled at least by laser abrasion means.

19. A filter for at least partially compensating for an X-ray tube target angle heel effect, comprising:
an anode side; and
a cathode side, wherein the cathode side has a higher attenuation coefficient than the anode side, wherein the attenuation coefficient is determined to at least partially compensate for the target angle heel effect; wherein the filter is from the same material as an anode plate of an X-ray source, and wherein the thickness deposition of the filter is controlled by mechanical, chemical and/or laser abrasion.

20. The filter of claim 19, where the material that the filter is from is tungsten alloy, where the filter has a horizontal top, where the filter is disposed on a flat window of an x-ray tube, where the filter is disposed such that the horizontal top and flat window touch along the horizontal top, where electrons travel from a cathode of the x-ray tube to an anode plate of the X-ray tube, where the material is sputtered on a film on the outside of the flat window such that the material is disposed on the flat window and forms the filter, where a section of the anode plate that experiences a collision from the electrons is not perpendicular with the cathode such that the electrons do not reflect from the anode plate at the same time, where the filter is of a single attenuation portion, and where a cathode side of the filter is about 200 μm thicker than an anode side of the filter.

* * * * *